(12) United States Patent
Zhao

(10) Patent No.: US 9,393,393 B2
(45) Date of Patent: Jul. 19, 2016

(54) METHOD FOR REDUCING TUMORS AND TRANSFORMING CANCER CELLS

(75) Inventor: Sihai Zhao, Jiangsu (CN)

(73) Assignees: HUAIBEI FENKUN HEALTH CONSULTANCY SERVICES CO., LTD., Xuzhou, Jiangsu (CN); Sihai Zhao, Xuzhou, Jiangsu (CN)

( * ) Notice: Subject to any disclaimer, the term of this patent is extended or adjusted under 35 U.S.C. 154(b) by 277 days.

(21) Appl. No.: 14/239,500

(22) PCT Filed: Sep. 12, 2012

(86) PCT No.: PCT/CN2012/081271
§ 371 (c)(1),
(2), (4) Date: Feb. 18, 2014

(87) PCT Pub. No.: WO2014/008708
PCT Pub. Date: Jan. 16, 2014

(65) Prior Publication Data
US 2014/0228812 A1    Aug. 14, 2014

(30) Foreign Application Priority Data
Jul. 12, 2012 (CN) .......................... 2012 1 0240554

(51) Int. Cl.
| | | |
|---|---|---|
| *A61K 36/00* | (2006.01) | |
| *A61M 37/00* | (2006.01) | |
| *A61K 36/8998* | (2006.01) | |
| *A23L 1/30* | (2006.01) | |
| *A23L 1/308* | (2006.01) | |
| *A61K 36/899* | (2006.01) | |
| *A61K 36/28* | (2006.01) | |
| *A61K 36/282* | (2006.01) | |
| *A23L 2/52* | (2006.01) | |
| *A61K 31/05* | (2006.01) | |
| *A61K 31/122* | (2006.01) | |
| *A61M 3/02* | (2006.01) | |

(52) U.S. Cl.
CPC .............. *A61M 37/00* (2013.01); *A23L 1/3002* (2013.01); *A23L 1/308* (2013.01); *A23L 1/3081* (2013.01); *A23L 2/52* (2013.01); *A61K 31/05* (2013.01); *A61K 31/122* (2013.01); *A61K 36/28* (2013.01); *A61K 36/282* (2013.01); *A61K 36/899* (2013.01); *A61K 36/8998* (2013.01); *A61M 3/02* (2013.01)

(58) Field of Classification Search
None
See application file for complete search history.

(56) References Cited

FOREIGN PATENT DOCUMENTS

| | | |
|---|---|---|
| CN | 1197651 A | 11/1998 |
| CN | 101133785 A | 3/2008 |
| CN | 101828700 A | 9/2010 |
| EP | 1702613 A | 9/2006 |
| WO | 2010/090498 A | 8/2010 |

*Primary Examiner* — Qiuwen Mi
(74) *Attorney, Agent, or Firm* — Novick, Kim & Lee, PLLC; Allen Xue

(57) ABSTRACT

This invention is related to a phenol-quinone therapy that shrinks tumors and transforms cancer cells. The therapy include four phases. In phase 1: cleansing poisons from the body, autologous melting, purifying five fluids, enhancing macro circulation, strengthening spirit. In phase 2: tuning qi in the body, fiber melting, purifying five qi, scavenging free radicals, enhance oxygen and vitality. In phase 3: nourishing the body, vitality melting, purifying the mind, enhancing micro circulation, enhancing immunity. And in phase 4: nourishing the body and blood, phenol-quinone melting, oxidizing tumors, transforming cancer cells, regenerating new cells. This therapeutic treatment method has little side effect. By changing the in vivo condition, it inhibits cancer cell growth and proliferation, enhances circulation inside human body, expels toxins accumulated in the human body, shrinks tumors, and transforms cancer cells. It results in curing cancer without using medicine and gives the patient a chance to live.

4 Claims, No Drawings

METHOD FOR REDUCING TUMORS AND TRANSFORMING CANCER CELLS

TECHNICAL FIELD

The present invention relates to a cancer therapy, especially of the therapy using phenols and quinones to melt and transform cancer tumor.

BACKGROUND

Cancer cells are the result of structural changes in healthy nucleus. They are transformed from the body's own healthy cells under a variety of external and internal factors. Cancer cells can continue to self-replicate and proliferation. Tumors are formed after the accumulation of hundreds of millions of cancer cells. The proliferation of cancer cells is not controllable by the self-immune mechanism inside the body. They are not needed in the body. Cancer cells cannot become mature and do not have any benefits or functions on the human body. They consume a large amount of nutrition due to their endless proliferation. Cancer cells may spread everywhere. Most of them grow invasively, damaging the normal structure and functions of nearby tissues and organs, resulting in various degrees of dysfunction.

There are more than 2000 kinds of naturally occurring phenolic compounds. They are the products of plant life. They play an important role in plant growth and development, immunity, anti-fungal, photosynthesis and respiration metabolism. Phenols and quinones like the breath and blood of the living plants. Growing plants contain phenols and quinones. Unheated living plants also contain phenols and quinones. Phenols and quinones are present in plants just like enzymes and chlorophyll are in the plants.

Phenol can carry plant gases and enzymes into the human body to absorb carbon dioxide and other waste gases and produce oxygen. Phenol in its gaseous form can also stop cancer cell metabolism and development. Quinone can carry plant liquids and chlorophyll into the human body and exchange liquid with human cells to produce fresh blood. Quinones can also dilute and restrict the carcinogens. They may also expel the diluted carcinogens from the human body. Phenols and quinones enter together into the human body can exchange chlorine, ammonia, methane, hydrogen sulfide and carbon dioxide to produce oxygen, blocking the passage of nutrients to the cancer cell. They may also convert the starved, anaerobic cancer cells into good cells that rely on oxygen. If phenols and quinones can jointly act on cancerous cells, they can be easily reduce tumor and transform cancerous cells, giving the patient a second opportunity to live.

SUMMARY OF INVENTION

In order to solve the problems of existing cancer therapy—severe side effects of cancer therapy and unable to completely cure the disease, the present invention provides a therapy that uses phenols and quinones to reduce tumor and transform cancerous cells. This method has little side effects. It changes the in vivo conditions in human body, effectively inhibits cancer cell growth and proliferation. It enhances circulation in the human body and discharge toxins accumulated in the human body. It reduces tumor and transforms cancerous cells. As a result, the cancer can be cured without medication and the patient may live.

The present invention provides the following technical scheme to solve the technical problem:

1. Treatment Location: One should choose a location with good air and water quality such as a resort area.

2. Mental preparation for the treatment: patients should change mentally, to gain peace of mind and do not get angry. The patient should be optimistic and not self-centered. He should live healthy and be resolute for the family and friends. He would become a useful again after rehabilitation. Then he would teach the method that cured him to others. The patient needs to be resolute and determined to complete the treatment during the treatment process. He should change his habits, his schedule, his diet. He should not eat anything rejected by the immune system—hot, cooked, and solid foods, and return to self, return to nature and follow the nature. He should act according to the biological clock, getting up at sunrise and going to bed at sun down, forming the healthy concept of self-healing.

3. Treatment methods: the treatment period of 128 days is divided into a total of four phases—cleansing, toning, nourishing, and healing. It also coincides with a metabolic cycle of human blood cells. The first phase is three days, which equals a metabolic cycle of human lip cells. The second phase is seven days, which equals a metabolic cycle of white blood cells in the immune system. The third phase is twenty-eight days, which is a metabolic cycle for the cells in lung, colon and skin. The fourth phase of ninety days equals a metabolic cycle for renal cells, bone marrow cells and hematopoietic stem cells.

The first phase: cleansing poisons from the body, washing the stomach and the intestines, clearing the passage, introducing phenols and quinones, strengthening the spirit. This phase lasts three days.

05:00 Get up, drink a glass of 10-50° C. water, 300-500 ml. Use the Mong Te Mei intestinal hydrotherapy instrument to rinse the intestines and to induce bowl movements, 20-40 minutes.

06:00 Add 200-400 ml boiled water to 1 gram of Pro-Health instant tea, and drink when it reaches 10-50° C.

07:00 Breakfast: add 200-400 ml, 10-50° C. warm water to 8 grams of Pro-Health Super Fiber, and drink with 0.9 grams Pro-Health Revita vitamin and 1.2 grams Pro-Health milk calcium.

08:00 With a pollution-free wheat and pollution-free natural water, use soilless cultivation method, to raise wheat seedlings of 6 cm or higher. Juice the seedlings with the root using Joyoung juicer, and drink immediately, discard the solids.

09:00 Juice 6 cm long wheat seedlings with roots and immediately drink 100-500 ml to flush colon 20-40 minutes.

10:00 Juice 6 cm long wheat seedlings with roots and immediately drink 100-500 ml, add 300-500 ml boiled water to 1 gram of instant tea, drink when it reaches 10-50° C.

11:00 Juice 6 cm long wheat seedlings with roots and immediately drink 100-500 ml, for lunch drink 10-50° C. boiled water 200-400 ml mixed with 8 grams Pro-Health Super Fiber with Pro-Health multifiber 5 grams and Pro-Health high calcium and fiber crackers 25 g.

12:00 Take a nap of 30 minutes to 2 hours between 11:00 to 13:00.

13:00 After the nap, drink boiled water 200-500 ml mixed with instant tea at 10-50° C. to flush colon 20-40 minutes.

14:00 Juice 6 cm long wheat seedlings with roots and immediately drink 100-500 ml.

15:00 Juice 6 cm long wheat seedlings with roots and immediately drink 100-500 ml, drink 300-500 ml boiled water mixed with 1 gram instant tea.

16:00 Juice 6 cm long wheat seedlings with roots and immediately drink 100-500 ml, drink 300-500 ml boiled water mixed with 1 gram instant tea.

17:00 Juice 6 cm long wheat seedlings with roots and immediately drink 100-500 ml, drink 300-500 ml boiled water mixed with 1 gram instant tea at 10-50° C. to flush colon 20-40 minutes.

18:00 Juice 6 cm long wheat seedlings with roots and immediately drink 100-500 ml.

19:00 Juice 6 cm long wheat seedlings with roots and immediately drink 100-500 ml. Dinner: use 10-50° C., 200-400 ml boiled water, mix it with Pro-Health Super Fiber 8 grams, drink with 0.9 gram Pro-Health Revita vitamin.

20:00 Juice 6 cm long barley seedlings with roots and immediately drink 50-300 ml. With a pollution-free barley and pollution-free natural water, use soilless cultivation method, to raise barley seedlings of 6 cm of more in length. Juice the seedlings using Joyoung juicer, and drink immediately, discard the solids.

21:00 Juice 6 cm long barley seedlings with roots and immediately drink 50-300 ml to flush colon 20-40 minutes.

22:00 Juice 6 cm long barley seedlings with roots and immediately drink 50-300 ml. Soak feet in a hot water bath having safflower 1 gram, mugwort 50 grams, ginger powder 50 grams, pepper powder 10 grams. Water depth is below the knee. Go to bed after sweating. It takes 20-40 minutes.

23:00 to 5:00 am must in deep sleep.

The second phase: adjusting qi in the body, purifying the lung, in vivo maintenance, vitality melting, aerobics add vitality. This stage last seven days.

05:00 Get up, drink a glass of 10-50° C. water, 300-500 ml. Use the Mong Te Mei intestinal hydrotherapy instrument to rinse the intestines and to induce bowl movements, 20-40 minutes.

06:00 Add 200-400 ml boiled water to 1 gram of Pro-Health instant tea, and drink when it reaches 10-50° C.

07:00 Breakfast: add 200-400 ml, 10-50° C. warm water to 8 grams of Pro-Health Super Fiber, and drink with 0.9 grams Pro-Health Revita Bao vitamin, 1.2 grams Pro-Health calcium syrup, and 2 grams of Pro-Health spirulina.

08:00 With a pollution-free sunflower seed and pollution-free natural water, use soilless cultivation method, to raise sunflower seedlings of 6 cm or higher. Juice the seedlings with the root using Joyoung juicer, and drink 50-300 ml juice immediately as a medicine, discard the solids.

09:00 Juice 6 cm long wheat seedlings with roots and immediately drink 100-500 ml to flush colon 20-40 minutes.

10:00 Juice 6 cm long wheat seedlings with roots and immediately drink 100-500 ml, add 300-500 ml boiled water to 1 gram of instant tea, drink when it reaches 10-50° C.

11:00 Juice 6 cm long wheat seedlings with roots and immediately drink 100-500 ml. In addition, juice 6 cm (or longer) sunflower seedlings and immediately drink 50-300 ml. For lunch drink 10-50° C. boiled water 200-400 ml mixed with 8 grams Pro-Health Super Fiber with Pro-Health multi-fiber 5 grams, Pro-Health high calcium and fiber crackers 25 g, and 2 grams of Pro-Health spirulina.

12:00 Take a nap of 30 minutes to 2 hours between 11:00 to 13:00.

13:00 After the nap drink boiled water 200-500 ml mixed with instant tea at 10-50° C. to flush colon 20-40 minutes.

14:00 Juice 6 cm long wheat seedlings with roots and immediately drink 100-500 ml.

15:00 Juice 6 cm long wheat seedlings with roots and immediately drink 100-500 ml, drink 300-500 ml boiled water mixed with 1 gram instant tea.

16:00 Juice 6 cm long wheat seedlings with roots and immediately drink 100-500 ml, drink 300-500 ml boiled water mixed with 1 gram instant tea.

17:00 Juice 6 cm long wheat seedlings with roots and immediately drink 100-500 ml, drink 300-500 ml boiled water mixed with 1 gram instant tea at 10-50° C. to flush colon 20-40 minutes.

18:00 Juice 6 cm long wheat seedlings with roots and immediately drink 100-500 ml.

19:00 Juice 6 cm long wheat seedlings with roots and immediately drink 100-500 ml. Dinner: use 10-50° C., 200-400 ml boiled water, mix it with Pro-Health Super Fiber 8 grams, drink with 0.9 gram Pro-Health Revita vitamin and 2 grams of Pro-Health spirulina.

20:00 Juice 6 cm long barley seedlings with roots and immediately drink 50-300 ml. With a pollution-free barley and pollution-free natural water, use soilless cultivation method, to raise barley seedlings of 6 cm of more in length. Juice the seedlings using Joyoung juicer, and drink immediately, discard the solids.

21:00 Juice 6 cm long barley seedlings with roots and immediately drink 50-300 ml to flush colon 20-40 minutes.

22:00 Juice 6 cm long barley seedlings with roots and immediately drink 50-300 ml. Soak feet in a hot water bath having safflower 1 gram, mugwort 50 grams, ginger powder 50 grams, pepper powder 10 grams. Water depth is below the knee. Go to bed after sweating. It takes 20-40 minutes.

23:00 to 5:00 am must in deep sleep.

The third phase: strengthening of the body, purifying the mind, and improving circulation, shrinking inside, enhancing immunity. This phase lasts 28 days.

05:00 Get up, drink a glass of 10-50° C. water, 300-500 ml. Use the Mong Te Mei intestinal hydrotherapy instrument to rinse the intestines and to induce bowl movements, 20-40 minutes.

06:00 Add 200-400 ml boiled water to 1 gram of Pro-Health instant tea, and drink when it reaches 10-50° C.

07:00 Breakfast: add 200-400 ml, 10-50° C. warm water to 8 grams of Pro-Health Super Fiber, and drink with 0.9 grams Pro-Health Revita Bao vitamin, 1.2 grams Pro-Health calcium syrup, 2 grams of Pro-Health spirulina, and 2 grams Pro-Health American ginseng, 1 gram of instant tea. In addition, juice sunflower seedlings of 6 cm or longer and drink 50-300 ml of the juice.

08:00 With a pollution-free sunflower seed and pollution-free natural water, use soilless cultivation method, to raise sunflower seedlings of 6 cm or higher. Juice the seedlings with the root using Joyoung juicer, and drink 50-300 ml juice immediately as a medicine, discard the solids.

09:00 Juice 6 cm long wheat seedlings with roots and immediately drink 100-500 ml to flush colon 20-40 minutes.

10:00 Juice 6 cm long wheat seedlings with roots and immediately drink 100-500 ml, add 300-500 ml boiled water to 1 gram of instant tea, drink when it reaches 10-50° C.

11:00 Juice 6 cm long wheat seedlings with roots and immediately drink 100-500 ml. In addition, juice 6 cm (or longer) sunflower seedlings and immediately drink 50-300 ml. For lunch drink 10-50° C. boiled water 200-400 ml mixed with 8 grams Pro-Health Super Fiber with Pro-Health multi-fiber 5 grams, Pro-Health High calcium and fiber crackers 25 g, 2 grams of Pro-Health spirulina, and 1 gram instant tea.

12:00 Take a nap of 30 minutes to 2 hours between 11:00 to 13:00.

13:00 After the nap, drink boiled water 200-500 ml mixed with instant tea at 10-50° C. to flush colon 20-40 minutes.

14:00 Juice 6 cm long wheat seedlings with roots and immediately drink 100-500 ml.

15:00 Juice 6 cm long wheat seedlings with roots and immediately drink 100-500 ml, drink 300-500 ml boiled water mixed with 1 gram instant tea.

16:00 Juice 6 cm long wheat seedlings with roots and immediately drink 100-500 ml, drink 300-500 ml boiled water mixed with 1 gram instant tea.

17:00 Juice 6 cm long wheat seedlings with roots and immediately drink 100-500 ml, drink 300-500 ml boiled water mixed with 1 gram instant tea at 10-50° C. to flush colon 20-40 minutes.

18:00 Juice 6 cm long wheat seedlings with roots and immediately drink 100-500 ml.

19:00 Juice 6 cm long wheat seedlings with roots and immediately drink 100-500 ml. Dinner: use 10-50° C., 200-400 ml boiled water, mix it with Pro-Health Super Fiber 8 grams, drink with 0.9 gram Pro-Health Revita vitamin, 2 grams of Pro-Health spirulina, and 1 gram instant tea.

20:00 Juice 6 cm long barley seedlings with roots and immediately drink 50-300 ml. With a pollution-free barley and pollution-free natural water, use soilless cultivation method, to raise barley seedlings of 6 cm of more in length. Juice the seedings using Joyoung juicer, and drink immediately, discard the solids.

21:00 Juice 6 cm long barley seedlings with roots and immediately drink 50-300 ml to flush colon 20-40 minutes.

22:00 Juice 6 cm long barley seedlings with roots and immediately drink 50-300 ml. Soak feet in a hot water bath having safflower 1 gram, mugwort 50 grams, ginger powder 50 grams, pepper powder 10 grams. Water depth is below the knee. Go to bed after sweating. It takes 20-40 minutes.

23:00 to 5:00 am must in deep sleep.

The fourth stage: nourishing the body and blood, enhancing microcirculation, shrinking the tumor, transforming cancer cells, regenerating new cells. This stage lasts 90 days.

05:00 Get up, drink a glass of 10-50° C. water, 300-500 ml. Use the Mong Te Mei intestinal hydrotherapy instrument to rinse the intestines and to induce bowl movements, 20-40 minutes.

06:00 Add 200-400 ml boiled water to 1 gram of Pro-Health instant tea, and drink when it reaches 10-50° C.

07:00 Breakfast: add 200-400 ml, 10-50° C. warm water to 8 grams of Pro-Health Super Fiber, and drink with 0.9 grams Pro-Health Revita vitamin, 1.2 grams Pro-Health milk calcium, 2 grams of Pro-Health spirulina, 2 grams Pro-Health American ginseng, 1 gram of instant tea, 2 gram Pro-Health Lecithin-E, and 2 grams Pro-Health Colostrum. In addition, juice sunflower seedlings of 6 cm or longer and drink 50-300 ml of the juice.

08:00 With a pollution-free sunflower seed and pollution-free natural water, use soilless cultivation method, to raise sunflower seedlings of 6 cm or higher. Juice the seedlings with the root using Joyoung juicer, and drink 50-300 ml juice immediately as a medicine, discard the solids.

09:00 Juice 6 cm long wheat seedlings with roots and immediately drink 100-500 ml to flush colon 20-40 minutes.

10:00 Juice 6 cm long wheat seedlings with roots and immediately drink 100-500 ml, add 300-500 ml boiled water to 1 gram of instant tea, drink when it reaches 10-50° C. Drink fresh oxygenated, pollution-free vegetable juices such as celery, apple, carrot, pear, cabbage and kiwi. Drink 200-500 ml immediately after juicing.

11:00 Juice 6 cm long wheat seedlings with roots and immediately drink 100-500 ml. In addition, juice 6 cm (or longer) sunflower seedlings and immediately drink 50-300 ml. For lunch drink 10-50° C. boiled water 200-400 ml mixed with 8 grams Pro-Health Super Fiber with Pro-Health multi-fiber 5 grams, Pro-Health High calcium and fiber crackers 25 g, 2 grams of Pro-Health spirulina, 1 gram instant tea, 2 gram Pro-Health Lecithin-E, and 2 grams Pro-Health Colostrum.

12:00 Take a nap of 30 minutes to 2 hours between 11:00 to 13:00.

13:00 After the nap, drink boiled water 200-500 ml mixed with instant tea at 10-50° C. to flush colon 20-40 minutes.

14:00 Juice 6 cm long wheat seedlings with roots and immediately drink 100-500 ml.

15:00 Juice 6 cm long wheat seedlings with roots and immediately drink 100-500 ml, drink 300-500 ml boiled water mixed with 1 gram instant tea.

16:00 Juice 6 cm long wheat seedlings with roots and immediately drink 100-500 ml, drink 300-500 ml boiled water mixed with 1 gram instant tea. Drink fresh oxygenated, pollution-free vegetable juices such as celery, apple, carrot, pear, cabbage and kiwi. Drink 200-500 ml immediately after juicing.

17:00 Juice 6 cm long wheat seedlings with roots and immediately drink 100-500 ml, drink 300-500 ml boiled water mixed with 1 gram instant tea at 10-50° C. to flush colon 20-40 minutes.

18:00 Juice 6 cm long wheat seedlings with roots and immediately drink 100-500 ml.

19:00 Juice 6 cm long wheat seedlings with roots and immediately drink 100-500 ml. Dinner: use 10-50° C., 200-400 ml boiled water, mix it with Pro-Health Super Fiber 8 grams, drink with 0.9 gram Pro-Health Revita vitamin, 2 grams of Pro-Health spirulina, 1 gram instant tea, 2 gram Pro-Health Lecithin-E, and 2 grams Pro-Health Colostrum.

20:00 Juice 6 cm long barley seedlings with roots and immediately drink 50-300 ml. With a pollution-free barley and pollution-free natural water, use soilless cultivation method, to raise barley seedlings of 6 cm of more in length. Juice the seedings using Joyoung juicer, and drink immediately, discard the solids.

21:00 Juice 6 cm long barley seedlings with roots and immediately drink 50-300 ml to flush colon 20-40 minutes.

22:00 Juice 6 cm long barley seedlings with roots and immediately drink 50-300 ml. Soak feet in a hot water bath having safflower 1 gram, mugwort 50 grams, ginger powder 50 grams, pepper powder 10 grams. Water depth is below the knee. Go to bed after sweating. It takes 20-40 minutes.

23:00 to 5:00 am must in deep sleep.

The present invention has the beneficial effects in that the therapeutic treatment method has little side effect. By changing the in vivo condition, it inhibits cancer cell growth and proliferation, enhances circulation inside human body, expels toxins accumulated in the human body, shrinks tumors, and transforms cancer cells. It results in curing cancer without using medicine and gives the patient a chance to live.

EMBODIMENTS

1. Treatment Location: One should choose a location with good air and water quality such as a resort area.

2. Mental preparation for the treatment: patients should change mentally, to gain peace of mind and do not get angry. The patient should be optimistic and not self-centered. He should live healthy and be resolute for the family and friends. He would become a useful again after rehabilitation. Then he would teach the method that cured him to others. The patient needs to be resolute and determined to complete the treatment during the treatment process. He should change his habits, his schedule, his diet. He should not eat anything rejected by the immune system—hot, cooked, and solid foods, and return to self, return to nature and follow the nature. He should act according to the biological clock, getting up at sunrise and going to bed at sun down, forming the healthy concept of self-healing.

3. Treatment methods: the treatment period of 128 days is divided into a total of four phases—cleansing, toning, nourishing, and healing. It also coincides with a metabolic cycle of human blood cells. The first phase is three days, which equals a metabolic cycle of human lip cells. The second phase is seven days, which equals a metabolic cycle of white blood cells in the immune system. The third phase is twenty-eight days, which is a metabolic cycle for the cells in lung, colon and skin. The fourth phase of ninety days equals a metabolic cycle for renal cells, bone marrow cells and hematopoietic stem cells.

The first phase: cleansing poisons from the body, washing the stomach and the intestines, clearing the passage, introducing phenols and quinones, strengthening the spirit. This phase lasts three days.

05:00 Get up, drink a glass of 10-50° C. water, 300-500 ml. Use the Mong Te Mei intestinal hydrotherapy instrument to rinse the intestines and to induce bowl movements, 20-40 minutes.

06:00 Add 200-400 ml boiled water to 1 gram of Pro-Health instant tea, and drink when it reaches 10-50° C.

07:00 Breakfast: add 200-400 ml, 10-50° C. warm water to 8 grams of Pro-Health Super Fiber, and drink with 0.9 grams Pro-Health Revita vitamin and 1.2 grams Pro-Health milk calcium.

08:00 With a pollution-free wheat and pollution-free natural water, use soilless cultivation method, to raise wheat seedlings of 6 cm or higher. Juice the seedlings with the root using Joyoung juicer, and drink immediately, discard the solids.

09:00 Juice 6 cm long wheat seedlings with roots and immediately drink 100-500 ml to flush colon 20-40 minutes.

10:00 Juice 6 cm long wheat seedlings with roots and immediately drink 100-500 ml, add 300-500 ml boiled water to 1 gram of instant tea, drink when it reaches 10-50° C.

11:00 Juice 6 cm long wheat seedlings with roots and immediately drink 100-500 ml, for lunch drink 10-50° C. boiled water 200-400 ml mixed with 8 grams Pro-Health Super Fiber with Pro-Health multifiber 5 grams and Pro-Health high calcium and fiber crackers 25 g.

12:00 Take a nap of 30 minutes to 2 hours between 11:00 to 13:00.

13:00 After the nap, drink boiled water 200-500 ml mixed with instant tea at 10-50° C. to flush colon 20-40 minutes.

14:00 Juice 6 cm long wheat seedlings with roots and immediately drink 100-500 ml.

15:00 Juice 6 cm long wheat seedlings with roots and immediately drink 100-500 ml, drink 300-500 ml boiled water mixed with 1 gram instant tea.

16:00 Juice 6 cm long wheat seedlings with roots and immediately drink 100-500 ml, drink 300-500 ml boiled water mixed with 1 gram instant tea.

17:00 Juice 6 cm long wheat seedlings with roots and immediately drink 100-500 ml, drink 300-500 ml boiled water mixed with 1 gram instant tea at 10-50° C. to flush colon 20-40 minutes.

18:00 Juice 6 cm long wheat seedlings with roots and immediately drink 100-500 ml.

19:00 Juice 6 cm long wheat seedlings with roots and immediately drink 100-500 ml. Dinner: use 10-50° C., 200-400 ml boiled water, mix it with Pro-Health Super Fiber 8 grams, drink with 0.9 gram Pro-Health Revita vitamin.

20:00 Juice 6 cm long barley seedlings with roots and immediately drink 50-300 ml. With a pollution-free barley and pollution-free natural water, use soilless cultivation method, to raise barley seedlings of 6 cm of more in length. Juice the seedlings using Joyoung juicer, and drink immediately, discard the solids.

21:00 Juice 6 cm long barley seedlings with roots and immediately drink 50-300 ml to flush colon 20-40 minutes.

22:00 Juice 6 cm long barley seedlings with roots and immediately drink 50-300 ml. Soak feet in a hot water bath having safflower 1 gram, mugwort 50 grams, ginger powder 50 grams, pepper powder 10 grams. Water depth is below the knee. Go to bed after sweating. It takes 20-40 minutes.

23:00 to 5:00 am must in deep sleep.

The second phase: adjust qi in the body, purify the lung, in vivo maintenance, vitality melting, aerobics add vitality. This stage last seven days.

05:00 Get up, drink a glass of 10-50° C. water, 300-500 ml. Use the Mong Te Mei intestinal hydrotherapy instrument to rinse the intestines and to induce bowl movements, 20-40 minutes.

06:00 Add 200-400 ml boiled water to 1 gram of Pro-Health instant tea, and drink when it reaches 10-50° C.

07:00 Breakfast: add 200-400 ml, 10-50° C. warm water to 8 grams of Pro-Health Super Fiber, and drink with 0.9 grams Pro-Health Revita Bao vitamin, 1.2 grams Pro-Health calcium syrup, and 2 grams of Pro-Health spirulina.

08:00 With a pollution-free sunflower seed and pollution-free natural water, use soilless cultivation method, to raise sunflower seedlings of 6 cm or higher. Juice the seedlings with the root using Joyoung juicer, and drink 50-300 ml juice immediately as a medicine, discard the solids.

09:00 Juice 6 cm long wheat seedlings with roots and immediately drink 100-500 ml to flush colon 20-40 minutes.

10:00 Juice 6 cm long wheat seedlings with roots and immediately drink 100-500 ml, add 300-500 ml boiled water to 1 gram of instant tea, drink when it reaches 10-50° C.

11:00 Juice 6 cm long wheat seedlings with roots and immediately drink 100-500 ml. In addition, juice 6 cm (or longer) sunflower seedlings and immediately drink 50-300 ml. For lunch drink 10-50° C. boiled water 200-400 ml mixed with 8 grams Pro-Health Super Fiber with Pro-Health multifiber 5 grams, Pro-Health high calcium and fiber crackers 25 g, and 2 grams of Pro-Health spirulina.

12:00 Take a nap of 30 minutes to 2 hours between 11:00 to 13:00.

13:00 After the nap drink boiled water 200-500 ml mixed with instant tea at 10-50° C. to flush colon 20-40 minutes.

14:00 Juice 6 cm long wheat seedlings with roots and immediately drink 100-500 ml.

15:00 Juice 6 cm long wheat seedlings with roots and immediately drink 100-500 ml, drink 300-500 ml boiled water mixed with 1 gram instant tea.

16:00 Juice 6 cm long wheat seedlings with roots and immediately drink 100-500 ml, drink 300-500 ml boiled water mixed with 1 gram instant tea.

17:00 Juice 6 cm long wheat seedlings with roots and immediately drink 100-500 ml, drink 300-500 ml boiled water mixed with 1 gram instant tea at 10-50° C. to flush colon 20-40 minutes.

18:00 Juice 6 cm long wheat seedlings with roots and immediately drink 100-500 ml.

19:00 Juice 6 cm long wheat seedlings with roots and immediately drink 100-500 ml. Dinner: use 10-50° C., 200-400 ml boiled water, mix it with Pro-Health Super Fiber 8 grams, drink with 0.9 gram Pro-Health Revita vitamin and 2 grams of Pro-Health spirulina.

20:00 Juice 6 cm long barley seedlings with roots and immediately drink 50-300 ml. With a pollution-free barley and pollution-free natural water, use soilless cultivation method, to raise barley seedlings of 6 cm of more in length. Juice the seedlings using Joyoung juicer, and drink immediately, discard the solids.

21:00 Juice 6 cm long barley seedlings with roots and immediately drink 50-300 ml to flush colon 20-40 minutes.

22:00 Juice 6 cm long barley seedlings with roots and immediately drink 50-300 ml. Soak feet in a hot water bath having safflower 1 gram, mugwort 50 grams, ginger powder 50 grams, pepper powder 10 grams. Water depth is below the knee. Go to bed after sweating. It takes 20-40 minutes.

23:00 to 5:00 am must in deep sleep.

The third phase: strengthening of the body, purifying the mind, and improving circulation, shrinking inside, enhancing immunity. This phase lasts 28 days.

05:00 Get up, drink a glass of 10-50° C. water, 300-500 ml. Use the Mong Te Mei intestinal hydrotherapy instrument to rinse the intestines and to induce bowl movements, 20-40 minutes.

06:00 Add 200-400 ml boiled water to 1 gram of Pro-Health instant tea, and drink when it reaches 10-50° C.

07:00 Breakfast: add 200-400 ml, 10-50° C. warm water to 8 grams of Pro-Health Super Fiber, and drink with 0.9 grams Pro-Health Revita Bao vitamin, 1.2 grams Pro-Health calcium syrup, 2 grams of Pro-Health spirulina, and 2 grams Pro-Health American ginseng, 1 gram of instant tea. In addition, juice sunflower seedlings of 6 cm or longer and drink 50-300 ml of the juice.

08:00 With a pollution-free sunflower seed and pollution-free natural water, use soilless cultivation method, to raise sunflower seedlings of 6 cm or higher. Juice the seedlings with the root using Joyoung juicer, and drink 50-300 ml juice immediately as a medicine, discard the solids.

09:00 Juice 6 cm long wheat seedlings with roots and immediately drink 100-500 ml to flush colon 20-40 minutes.

10:00 Juice 6 cm long wheat seedlings with roots and immediately drink 100-500 ml, add 300-500 ml boiled water to 1 gram of instant tea, drink when it reaches 10-50° C.

11:00 Juice 6 cm long wheat seedlings with roots and immediately drink 100-500 ml. In addition, juice 6 cm (or longer) sunflower seedlings and immediately drink 50-300 ml. For lunch drink 10-50° C. boiled water 200-400 ml mixed with 8 grams Pro-Health Super Fiber with Pro-Health multi-fiber 5 grams, Pro-Health High calcium and fiber crackers 25 g, 2 grams of Pro-Health spirulina, and 1 gram instant tea.

12:00 Take a nap of 30 minutes to 2 hours between 11:00 to 13:00.

13:00 After the nap, drink boiled water 200-500 ml mixed with instant tea at 10-50° C. to flush colon 20-40 minutes.

14:00 Juice 6 cm long wheat seedlings with roots and immediately drink 100-500 ml.

15:00 Juice 6 cm long wheat seedlings with roots and immediately drink 100-500 ml, drink 300-500 ml boiled water mixed with 1 gram instant tea.

16:00 Juice 6 cm long wheat seedlings with roots and immediately drink 100-500 ml, drink 300-500 ml boiled water mixed with 1 gram instant tea.

17:00 Juice 6 cm long wheat seedlings with roots and immediately drink 100-500 ml, drink 300-500 ml boiled water mixed with 1 gram instant tea at 10-50° C. to flush colon 20-40 minutes.

18:00 Juice 6 cm long wheat seedlings with roots and immediately drink 100-500 ml.

19:00 Juice 6 cm long wheat seedlings with roots and immediately drink 100-500 ml. Dinner: use 10-50° C., 200-400 ml boiled water, mix it with Pro-Health Super Fiber 8 grams, drink with 0.9 gram Pro-Health Revita vitamin, 2 grams of Pro-Health spirulina, and 1 gram instant tea.

20:00 Juice 6 cm long barley seedlings with roots and immediately drink 50-300 ml. With a pollution-free barley and pollution-free natural water, use soilless cultivation method, to raise barley seedlings of 6 cm of more in length. Juice the seedlings using Joyoung juicer, and drink immediately, discard the solids.

21:00 Juice 6 cm long barley seedlings with roots and immediately drink 50-300 ml to flush colon 20-40 minutes.

22:00 Juice 6 cm long barley seedlings with roots and immediately drink 50-300 ml. Soak feet in a hot water bath having safflower 1 gram, mugwort 50 grams, ginger powder 50 grams, pepper powder 10 grams. Water depth is below the knee. Go to bed after sweating. It takes 20-40 minutes.

23:00 to 5:00 am must in deep sleep.

The fourth stage: nourishing the body and blood, enhancing microcirculation, shrinking the tumor, transforming cancer cells, regenerating new cells. This stage lasts 90 days.

05:00 Get up, drink a glass of 10-50° C. water, 300-500 ml. Use the Mong Te Mei intestinal hydrotherapy instrument to rinse the intestines and to induce bowl movements, 20-40 minutes.

06:00 Add 200-400 ml boiled water to 1 gram of Pro-Health instant tea, and drink when it reaches 10-50° C.

07:00 Breakfast: add 200-400 ml, 10-50° C. warm water to 8 grams of Pro-Health Super Fiber, and drink with 0.9 grams Pro-Health Revita vitamin, 1.2 grams Pro-Health milk calcium, 2 grams of Pro-Health spirulina, 2 grams Pro-Health American ginseng, 1 gram of instant tea, 2 gram Pro-Health Lecithin-E, and 2 grams Pro-Health Colostrum. In addition, juice sunflower seedlings of 6 cm or longer and drink 50-300 ml of the juice.

08:00 With a pollution-free sunflower seed and pollution-free natural water, use soilless cultivation method, to raise sunflower seedlings of 6 cm or higher. Juice the seedlings with the root using Joyoung juicer, and drink 50-300 ml juice immediately as a medicine, discard the solids.

09:00 Juice 6 cm long wheat seedlings with roots and immediately drink 100-500 ml to flush colon 20-40 minutes.

10:00 Juice 6 cm long wheat seedlings with roots and immediately drink 100-500 ml, add 300-500 ml boiled water to 1 gram of instant tea, drink when it reaches 10-50° C. Drink fresh oxygenated, pollution-free vegetable juices such as celery, apple, carrot, pear, cabbage and kiwi. Drink 200-500 ml immediately after juicing.

11:00 Juice 6 cm long wheat seedlings with roots and immediately drink 100-500 ml. In addition, juice 6 cm (or longer) sunflower seedlings and immediately drink 50-300 ml. For lunch drink 10-50° C. boiled water 200-400 ml mixed with 8 grams Pro-Health Super Fiber with Pro-Health multi-fiber 5 grams, Pro-Health High calcium and fiber crackers 25 g, 2 grams of Pro-Health spirulina, 1 gram instant tea, 2 gram Pro-Health Lecithin-E, and 2 grams Pro-Health Colostrum.

12:00 Take a nap of 30 minutes to 2 hours between 11:00 to 13:00.

13:00 After the nap, drink boiled water 200-500 ml mixed with instant tea at 10-50° C. to flush colon 20-40 minutes.

14:00 Juice 6 cm long wheat seedlings with roots and immediately drink 100-500 ml.

15:00 Juice 6 cm long wheat seedlings with roots and immediately drink 100-500 ml, drink 300-500 ml boiled water mixed with 1 gram instant tea.

16:00 Juice 6 cm long wheat seedlings with roots and immediately drink 100-500 ml, drink 300-500 ml boiled water mixed with 1 gram instant tea. Drink fresh oxygenated, pollution-free vegetable juices such as celery, apple, carrot, pear, cabbage and kiwi. Drink 200-500 ml immediately after juicing.

17:00 Juice 6 cm long wheat seedlings with roots and immediately drink 100-500 ml, drink 300-500 ml boiled water mixed with 1 gram instant tea at 10-50° C. to flush colon 20-40 minutes.

18:00 Juice 6 cm long wheat seedlings with roots and immediately drink 100-500 ml.

19:00 Juice 6 cm long wheat seedlings with roots and immediately drink 100-500 ml. Dinner: use 10-50° C., 200-400 ml boiled water, mix it with Pro-Health Super Fiber8 grams, drink with 0.9 gram Pro-Health Revita vitamin, 2 grams of Pro-Health spirulina, 1 gram instant tea, 2 gram Pro-Health Lecithin-E, and 2 grams Pro-Health Colostrum.

20:00 Juice 6 cm long barley seedlings with roots and immediately drink 50-300 ml. With a pollution-free barley and pollution-free natural water, use soilless cultivation method, to raise barley seedlings of 6 cm of more in length. Juice the seedings using Joyoung juicer, and drink immediately, discard the solids.

21:00 Juice 6 cm long barley seedlings with roots and immediately drink 50-300 ml to flush colon 20-40 minutes.

22:00 Juice 6 cm long barley seedlings with roots and immediately drink 50-300 ml. Soak feet in a hot water bath having safflower 1 gram, mugwort 50 grams, ginger powder 50 grams, pepper powder 10 grams. Water depth is below the knee. Go to bed after sweating. It takes 20-40 minutes.

23:00 to 5:00 am must in deep sleep.

Example 1

Han Li, female, born Sep. 12, 1989, now living in Pei County in Jiangsu province, self-employed in restaurant business.

Case: Feb. 1, 2012, Pei County People's Hospital Inspection Report: on both sides of a large pleural effusion, inflammation of the lungs.

Feb. 2, 2012, checked into Xuzhou Medical College Hospital (see test report for details). Received dialysis once every 2-3 days during hospitalization.

Feb. 16, 2012, discharge orders: blood work after three days, and the family was told that it would be difficult to live beyond two months.

On Feb. 16, 2012, the day of discharge, the family rushed her to the East China Sea Hot Spring Penghu Bay Spa. The patient was frail and was helped by others into the room. Started to receive phenol-quinone treatment method and kept a good performance during recuperation. On Mar. 6, 2012, returned to Xuzhou No. 2 Hospital for check-up after improvement. No need for further dialysis. Prior to her admission into the East China Sea Hot Spring Penghu Bay Spa, the doctor predicted two-month life expectancy, and was carried into the room by others. She was nursed back to health and returned home full of joy. She is still healthy.

Example 2

Haohong Ru, male, born in 1963, farmer, now living in Panggezhuang, Beijing.

Case: Sep. 3, 2011, at that time his height is 180 cm, weight 103.6 kg, slightly obese, high blood pressure, low potassium levels, high triglycerides, high cholesterol, loss of sexual function, dizziness, tinnitus, cervical pain, indigestion, gout, leg pain, limb weakness, sleep snoring, leg cramps, hemorrhoids, blood in the stool, urine endless, nose bleeding, and sometimes loose stools, sometimes constipation, skin wet, big loss of calcium, cerebral blood oxygen deficiency, proptosis purple, blue lips, and typical acidic in vivo condition and sub-health.

Sep. 3, 2011, he moved from Beijing to to Ningguo in Anhui province. It has a beautiful environment and good water quality, free of air pollution. He received phenol-quinone treatment. After one month, most of the symptoms disappeared. He moved back to his hometown on Oct. 2, 2011, and is now recovered.

Example 3

Xia Kun, female, 28 years old, married, farmer.
Admission diagnosis: hepatocellular carcinoma,
Admission date: 20 Dec. 2011
Name of the procedure: hepatic arterial chemoembolization
Surgery Date: Dec. 26, 2011
Discharge diagnosis: hepatocellular carcinoma
Discharge date: Jan. 9, 2012
Admission situations: Xia Kun, female, 28 years old, main complaint at the admission "a mass in upper abdominal, felt pain for a month."

Once again, Xuzhou Medical College Hospital discharge records:
Admission diagnosis: intervention in patients with liver cancer
Admission Date: Feb. 21, 2012
Name of the procedure: hepatic arterial chemoembolization
Surgery Date: Feb. 21, 2012
Discharge diagnosis: after surgery for hepatocellular carcinoma
Discharge date: Mar. 2, 2012
Admission situations: patients Xia Kun, young women, mainly due to "two months after surgery for primary liver cancer."

Hospital admission test: AFP 3000:00↑, Feb. 22, 2012, after two surgeries to over 3000, the treatment ineffective, doctors predicted life expectancy of three months. The same hospital in Mar. 1, 2012 again carried out a diagnose. AFP 2577:00↑. The treatment ineffective, doctors predicted life expectancy of two months.

In such desperate circumstances, patients and their families have a glimmer of hope and admitted into the East China Sea Hot Spring Penghu Bay Spa to receive the phenol-quinone therapy that having four phases from Mar. 23, 2013 to Apr. 4, 2012. Afterwards received report from the Donghai County People's Hospital. AFP 74.86:00↑. The patient and her family are very happy. Currently, the patient's physical condition gradually restored and she is able to take care of herself.

There are 21 patients like the cases described above from 2009 to the present. Among them three cases the patients died because of failing to adhere to the phenol-quinone therapy, which led to worsening of the situation. There are two cases in which the patients are still receiving the therapy. Their conditions are gradually improving and the body functions are recovering. In 16 cases, after careful treatment using the phenol-quinone therapy for 1-3 months, the patients have been cured. Afterwards the patients not only can take care of themselves but may also carry out certain jobs.

What is claimed is:
1. A method for treating cancer, comprising treating a patient in need thereof consecutively in Phase 1, Phase 2, Phase 3, and Phase 4,
wherein the Phase 1 treatment lasts for three days, the Phase 2 treatment lasts for seven days, the Phase 3 treatment for twenty eight days, and the Phase 4 treatment for ninety days, wherein the Phase 1 treatment comprises:
drinking 300-500 ml of water at 10-50° C. after getting up at 05:00;
drinking 200-400 ml of tea brewed using 1 gram of Pro-Health instant tea at 10-50° C. at 06:00;
drinking or eating 8 grams Pro-Health Super Fiber with 200-400 ml water at 10-50° C., 0.9 grams Pro-Health Revita vitamin, and 1.2 grams Pro-Health calcium milk at 07:00;
drinking 50-300 ml of a wheat seedling juice at 08:00, wherein the wheat seedlings juice is made in a juicer using wheat seedlings that are 6 cm or longer and are cultivated soilless with pollution-free water;
drinking 100-500 ml of the wheat seedling juice at 09:00;
drinking 100-500 ml of the wheat seedling juice and 300-500 ml tea brewed with 1 gram of Pro-Health instant tea at 10-50° C. at 10:00;
drinking or eating 100-500 ml of the wheat seedling juice, 8 grams Pro-Health Super Fiber, 5 grams Pro-Health multifiber, and 25 grams Pro-Health high calcium and fiber crackers with 200-400 ml boiled water at 10-50° C. at 11:00;
napping for 30 minutes to 2 hours starting 12:00;
drinking 200-500 ml brewed Pro-Health tea at 10-50° C. at 13:00;
drinking 100-500 ml of the wheat seedling juice at 14:00;
drinking 100-500 ml of the wheat seedling juice and 300-500 ml tea brewed with 1 gram Pro-Health instant tea at 15:00;
drinking 100-500 ml of the wheat seedling juice and 300-500 ml tea brewed with 1 gram Pro-Health instant tea at 16:00;
drinking 100-500 ml of the wheat seedling juice and 300-500 ml tea brewed with 1 gram Pro-Health instant tea at 17:00;
drinking 100-500 ml of the wheat seedling juice at 18:00;
drinking or eating 100-500 ml of the wheat seedling juice, 8 grams Pro-Health Super Fiber, 0.9 gram Pro-Health Revita vitamin with 200-400 boiled water at 19:00;
drinking 50-300 ml of a barely seedling juice at 20:00, wherein the barely seedlings juice is made in a juicer using barely seedlings that are 6 cm or longer and are cultivated soilless with pollution-free water;
drinking 50-300 ml of the barely seedling juice at 21:00;
drinking or eating 50-300 ml of the barely seedling juice, soaking feet in a hot water bath having 1 gram safflower, 50 grams mugwort, 50 grams ginger powder, and 10 grams pepper powder for 20-40 minutes at 22:00 before going to bed; and
being in a deep sleep between 23:00 to 05:00 am.

2. The method of claim 1, wherein the Phase 2 treatment comprises:
drinking 300-500 ml of water at 10-50° C. after getting up at 05:00;
drinking 200-400 ml of tea brewed using 1 gram of Pro-Health instant tea at 10-50° C. at 06:00;
drinking or eating 8 grams Pro-Health Super Fiber with 200-400 ml water at 10-50° C., 0.9 grams Pro-Health Revita vitamin, and 1.2 grams Pro-Health calcium milk, and 2 grams Pro-Health spirulina at 07:00;
drinking 50-300 ml of a sunflower seedling juice at 08:00, wherein the sunflower seedlings juice is made in a juicer using sunflower seedlings that are 6 cm or longer and are cultivated soilless with pollution-free water;
drinking 100-500 ml of the wheat seedling juice at 09:00;
drinking 100-500 ml of the wheat seedling juice and 300-500 ml tea brewed with 1 gram of Pro-Health instant tea at 10-50° C. at 10:00;
drinking or eating 100-500 ml of the wheat seedling juice, 300-500 ml of the sunflower seedling juice, 8 grams Pro-Health Super Fiber, 5 grams Pro-Health multifiber, and 25 grams Pro-Health high calcium and fiber crackers with 200-400 ml boiled water at 10-50° C. at 11:00;
napping for 30 minutes to 2 hours starting 12:00;
drinking 200-500 ml brewed Pro-Health tea at 10-50° C. at 13:00;
drinking 100-500 ml of the wheat seedling juice at 14:00;
drinking 100-500 ml of the wheat seedling juice and 300-500 ml tea brewed with 1 gram Pro-Health instant tea at 15:00;
drinking 100-500 ml of the wheat seedling juice and 300-500 ml tea brewed with 1 gram Pro-Health instant tea at 16:00;
drinking 100-500 ml of the wheat seedling juice and 300-500 ml tea brewed with 1 gram Pro-Health instant tea at 10-50° C. at 17:00;
drinking 100-500 ml of the wheat seedling juice at 18:00;
drinking or eating 100-500 ml of the wheat seedling juice, 8 grams Pro-Health Super Fiber, 0.9 gram Pro-Health Revita vitamin, 2 gram Pro-Health spirulina with 200-400 boiled water at 19:00;
drinking 50-300 ml of the barely seedling juice at 20:00;
drinking 50-300 ml of the barely seedling juice at 21:00;
drinking or eating 50-300 ml of the barely seedling juice, soaking feet in the hot water bath 20-40 minutes at 22:00 before going to bed; and
being in a deep sleep between 23:00 to 05:00.

3. The method of claim 2, wherein the Phase 3 treatment comprises:
drinking 300-500 ml of water at 10-50° C. after getting up at 05:00;
drinking 200-400 ml of tea brewed using 1 gram of Pro-Health instant tea at 10-50° C. at 06:00;
drinking or eating 8 grams Pro-Health Super Fiber with 200-400 ml water at 10-50° C., 0.9 grams Pro-Health Revita vitamin, and 1.2 grams Pro-Health calcium milk, 2 grams Pro-Health spirulina, 2 grams Pro-Health American ginseng, 1 gram of Pro-Health instant tea, and 50-300 ml of the sunflower seedling juice at 07:00;
drinking 50-300 ml of the sunflower seedling juice at 08:00;
drinking 100-500 ml of the wheat seedling juice at 09:00;
drinking 100-500 ml of the wheat seedling juice and 300-500 ml tea brewed with 1 gram of Pro-Health instant tea at 10-50° C. at 10:00;
drinking or eating 100-500 ml of the wheat seedling juice, 300-500 ml of the sunflower seedling juice, 8 grams Pro-Health Super Fiber, 5 grams Pro-Health multifiber, and 25 grams Pro-Health high calcium and fiber crackers, 2 grams Pro-Health spirulina, and 1 gram of instant tea at 11:00;
napping for 30 minutes to 2 hours starting 12:00;
drinking 200-500 ml brewed Pro-Health tea at 10-50° C. at 13:00;
drinking 100-500 ml of the wheat seedling juice at 14:00;
drinking 100-500 ml of the wheat seedling juice and 300-500 ml tea brewed with 1 gram Pro-Health instant tea at 15:00;
drinking 100-500 ml of the wheat seedling juice and 300-500 ml tea brewed with 1 gram Pro-Health instant tea at 16:00;

drinking 100-500 ml of the wheat seedling juice and 300-500 ml tea brewed with 1 gram Pro-Health instant tea at 10-50° C. at 17:00;

drinking 100-500 ml of the wheat seedling juice at 18:00;

drinking or eating 100-500 ml of the wheat seedling juice, 8 grams Pro-Health Super Fiber, 0.9 gram Pro-Health Revita vitamin, 2 gram Pro-Health spirulina, 1 gram instant tea with 200-400 boiled water at 19:00;

drinking 50-300 ml of the barely seedling juice at 20:00;

drinking 50-300 ml of the barely seedling juice at 21:00;

drinking or eating 50-300 ml of the barely seedling juice, soaking feet in the hot water bath 20-40 minutes at 22:00 before going to bed; and being in a deep sleep between 23:00 to 05:00.

4. The method of claim 3, wherein the Phase 4 treatment comprises:

drinking 300-500 ml of water at 10-50° C. after getting up at 05:00;

drinking 200-400 ml of tea brewed using 1 gram of Pro-Health instant tea at 10-50° C. at 06:00;

drinking or eating 8 grams Pro-Health Super Fiber, 0.9 grams Pro-Health Revita vitamin, and 1.2 grams Pro-Health calcium milk, and 2 grams Pro-Health spirulina, 2 grams American ginseng, 1 gram instant tea, 2 gram Pro-Health Lecithin-E, and 2 grams Pro-Health Colostrum with 200-400 ml water at 10-50° C., and 50-300 ml of the sunflower seedling juice at 07:00;

drinking 50-300 ml of a sunflower seedling juice at 08:00;

drinking 100-500 ml of the wheat seedling juice at 09:00;

drinking 100-500 ml of the wheat seedling juice and 300-500 ml tea brewed with 1 gram of Pro-Health instant tea at 10-50° C. at 10:00;

drinking or eating 100-500 ml of the wheat seedling juice, 300-500 ml of the sunflower seedling juice, 8 grams Pro-Health Super Fiber, 5 grams Pro-Health multifiber, and 25 grams Pro-Health high calcium and fiber crackers, 2 gram Pro-Health spirulina, 1 gram Pro-Health instant tea, 2 gram Pro-Health Lecithin-E, and 2 grams Pro-Health Colostrum with 200-400 ml boiled water at 10-50° C. at 11:00;

napping for 30 minutes to 2 hours starting 12:00;

drinking 200-500 ml brewed Pro-Health tea at 10-50° C. at 13:00;

drinking 100-500 ml of the wheat seedling juice at 14:00;

drinking 100-500 ml of the wheat seedling juice and 300-500 ml tea brewed with 1 gram Pro-Health instant tea at 15:00;

drinking 100-500 ml of the wheat seedling juice, 300-500 ml tea brewed with 1 gram Pro-Health instant tea, and a vegetable juice chosen from a celery just, an apple juice, a carrot juice, a pear juice, a cabbage juice, and a kiwi juice at 16:00;

drinking 100-500 ml of the wheat seedling juice and 300-500 ml tea brewed with 1 gram Pro-Health instant tea at 10-50° C. at 17:00;

drinking 100-500 ml of the wheat seedling juice at 18:00;

drinking or eating 100-500 ml of the wheat seedling juice, 8 grams Pro-Health Super Fiber, 0.9 gram Pro-Health Revita vitamin, 2 gram Pro-Health spirulina, 1 gram Pro-Health instant tea, 2 grams Pro-Health Lecithin-E, and 2 grams Pro-Health Colostrum with 200-400 boiled water at 19:00;

drinking 50-300 ml of the barely seedling juice at 20:00;

drinking 50-300 ml of the barely seedling juice at 21:00;

drinking or eating 50-300 ml of the barely seedling juice, soaking feet in the hot water bath 20-40 minutes at 22:00 before going to bed; and being in a deep sleep between 23:00 to 05:00.

* * * * *